US00RE50049E

(19) United States
(12) Reissued Patent
Chaudhuri et al.

(10) Patent Number: US RE50,049 E
(45) Date of Reissued Patent: Jul. 23, 2024

(54) COMPOSITIONS AND METHODS FOR TREATING PSORIASIS

(71) Applicant: SYMBIONYX PHARMACEUTICALS INC, Boonton, NJ (US)

(72) Inventors: Ratan K Chaudhuri, Lincoln Park, NJ (US); Krys Bojanowski, Santa Paula, CA (US)

(73) Assignee: Sytheon Ltd., Parsippany, NJ (US)

(21) Appl. No.: 17/359,639

(22) Filed: Jun. 28, 2021

Related U.S. Patent Documents

Reissue of:
(64) Patent No.: 9,636,321
Issued: May 2, 2017
Appl. No.: 15/081,898
Filed: Mar. 27, 2016

U.S. Applications:
(60) Provisional application No. 62/139,619, filed on Mar. 27, 2015.

(51) Int. Cl.

| | |
|---|---|
| ***A61K 31/341*** | (2006.01) |
| ***A61K 9/00*** | (2006.01) |
| ***A61K 31/34*** | (2006.01) |
| ***A61K 45/06*** | (2006.01) |
| ***C07D 493/04*** | (2006.01) |

(52) U.S. Cl.
CPC ..... *A61K 31/341* (2013.01); *A61K 9/0014* (2013.01); *A61K 9/0053* (2013.01); *A61K 31/34* (2013.01); *A61K 45/06* (2013.01); *C07D 493/04* (2013.01)

(58) Field of Classification Search
CPC .. A61K 31/341; A61K 9/0014; A61K 9/0053; A61K 31/34; A61K 45/06; C07D 493/04
See application file for complete search history.

(56) References Cited

U.S. PATENT DOCUMENTS

| | | | | |
|---|---|---|---|---|
| 2,234,200 | A | 3/1941 | Soltzberg | |
| 2,420,519 | A | 5/1947 | Brown | |
| 4,169,152 | A | 9/1979 | LeMaistre et al. | |
| 4,293,565 | A | 10/1981 | Cordes et al. | |
| 4,297,290 | A | 10/1981 | Stockburger | |
| 4,322,359 | A | 3/1982 | Hillard et al. | |
| 4,364,953 | A | 12/1982 | Klessing et al. | |
| 4,419,522 | A | 12/1983 | Elekes et al. | |
| 4,420,470 | A | 12/1983 | Otsuka et al. | |
| 4,435,586 | A | 3/1984 | Kruse et al. | |
| 4,559,351 | A | 12/1985 | Stoss et al. | |
| 4,627,976 | A | 12/1986 | Lynch | |
| 4,659,846 | A | 4/1987 | Maurer et al. | |
| 4,769,379 | A | 9/1988 | Leitold et al. | |
| 4,770,871 | A | 9/1988 | Greenshields | |
| 4,806,542 | A | 2/1989 | Stoss et al. | |
| 4,851,439 | A | 7/1989 | Speiser et al. | |
| RE33,748 | E | 11/1991 | Meyborg et al. | |
| 5,837,669 | A | 11/1998 | Petit et al. | |
| 6,395,810 | B1 | 5/2002 | Luitjes et al. | |
| 6,433,024 | B1 | 8/2002 | Popp et al. | |
| 6,693,209 | B2 | 2/2004 | Van Es et al. | |
| 7,115,252 | B2 | 10/2006 | Hodosh | |
| 8,129,549 | B2 | 3/2012 | Fuertes et al. | |
| 8,389,465 | B2 | 3/2013 | Breffa et al. | |
| 8,445,705 | B2 | 5/2013 | Howard et al. | |
| 8,496,917 | B2 | 7/2013 | Chaudhuri | A61K 8/498 424/59 |
| 9,062,069 | B2 | 6/2015 | Benattar et al. | |
| 9,358,199 | B2 | 6/2016 | Pilz et al. | |
| 9,445,595 | B2 | 9/2016 | Pilz et al. | |
| 9,555,117 | B2 | 1/2017 | Pilz et al. | |
| 9,644,059 | B2 | 5/2017 | Palmese et al. | |
| 10,179,118 | B2 | 1/2019 | Karaborni et al. | |
| 2008/0293807 | A1 | 11/2008 | Miura et al. | |
| 2011/0046182 | A1 | 2/2011 | Gilmer et al. | |
| 2011/0117036 | A1 | 5/2011 | Chaudhuri | |
| 2011/0196161 | A1 | 8/2011 | Fuertes et al. | |
| 2014/0249285 | A1 | 9/2014 | Palmese et al. | |
| 2014/0323564 | A1 | 10/2014 | Pilz et al. | |
| 2015/0274861 | A1 | 10/2015 | Chen et al. | |

FOREIGN PATENT DOCUMENTS

| | | | |
|---|---|---|---|
| DE | 19723732 | A1 | 12/1998 |
| EP | 0065267 | A2 | 11/1982 |
| EP | 0234494 | A2 | 9/1987 |
| EP | 2174641 | A1 | 4/2010 |
| GB | 613444 | | 11/1948 |
| GB | 2358859 | B | 10/2003 |
| JP | 59-175408 | A | 10/1984 |
| WO | 9817673 | A1 | 4/1998 |
| WO | 01/85159 | A1 | 11/2001 |
| WO | 2008/155159 | A1 | 12/2008 |

(Continued)

OTHER PUBLICATIONS

National institute for Health Research, "Dimethyl fumarate for plaque psoriasis", NIHR HSC ID: 7758, Nov. 2013.

Naves, A,F, et al., "Enzymatic Synthesis of Unsaturated Polyesters Based on Isosorbide and Isomannide", J. Polymer Science, Part A, Polymer Chemistry 2013, 51, 3881-3891.

Mayo Clinic. "Psoriasis." © 2016. Available from: < http://www.mayoclinic.org/diseases-conditions/psoriasis/basics/definition/CON-20030838?p=1 >.*

National Psoriasis Foundation. "Psoriasis Treatments." © 2016. Available from: < https://www.psoriasis.org/about-psoriasis/treatments >.*

Zenner, M.D., et al. "Unexpected Tackifiers from Isosorbide." ChemSusChem. (2015), vol. 8, pp. 448-451.*

Stoss, P., et. al., "1,4:3,6-Dianhydrohexitols", Advances in Carbohydrate Chemistry and Biochemistry,vol. 49, pp. 93, 168-169, 1991.

Trahanovsky, W.S., et. al., "Isosorbide Esters;Enantiopure Alcholos Derived From Glucose", Fuel Chemistry Div. Preprints, 47(1), pp. 368-369, 2002.

(Continued)

*Primary Examiner* — Jerry D Johnson
(74) *Attorney, Agent, or Firm* — Hoffmann & Baron LLP; Edward K. Welch, II

(57) ABSTRACT

Novel isohexides and pharmaceutical compositions containing the same as well as methods of using the same in the treatment of psoriasis.

22 Claims, 2 Drawing Sheets

(56) References Cited

FOREIGN PATENT DOCUMENTS

| | | | |
|---|---|---|---|
| WO | 2012098237 | A1 | 7/2012 |
| WO | 2013001192 | A1 | 1/2013 |
| WO | 2013/017257 | A1 | 2/2013 |
| WO | 2013/017260 | A1 | 2/2013 |
| WO | 2013/041388 | A1 | 3/2013 |
| WO | 2013/066461 | A1 | 5/2013 |
| WO | 2013066461 | A2 | 5/2013 |
| WO | 2014/062625 | A1 | 4/2014 |

OTHER PUBLICATIONS

Chatti, S., et. al., "Cation and Leaving Group Effects in Isosorbide Alkylation Under Microwave in Phase Transfer Catalysis," Tetrahedron 57, pp. 4365-4370, 2001.

Zenner et. al., "Unexpected Tackifers from Isosorbide," ChemSusChem 8(3): 448-451, 2015.

International Search Report and Written Opinion for corresponding International PCT Patent Application No. PCT/US2016/024392.

"Cure/definition of cure by Medical Dictionary", http://medical-dictionary.thefreedictionary.come/cure, Dec. 6, 2016.

"Therapeutic/definition of therapuetic by Medical Dictionary", http://medical-dictionary.thefreedictionary.come/therapuetic, Dec. 13, 2016.

* cited by examiner

COMPOSITIONS AND METHODS FOR TREATING PSORIASIS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application *is an application for reissue of U.S. Pat. No. 9,636,321 B2, issued May 2, 2017, which* claims the benefit of U.S. Provisional Patent Application No. 62/139,619 filed Mar. 27, 2015, the contents of which are incorporated herein by reference in their entirety.

TECHNICAL FIELD

The present teaching is directed to new isosorbide compounds and compositions and methods of using the same in the treatment of psoriasis and other diseases having similar and/or common disease specific gene expressions.

BACKGROUND

Psoriasis is a chronic complex disease, characterized by hyperproliferation of keratinocytes and increased dermal infiltration by immune cells, notably neutrophils and Th1/Th17 cells (R Heidenrich et al., Angiogenesis drives psoriasis pathogenesis, Int J Exp Pathol, 90(3):232-248, 2009) which affects about 2-4% of caucasian population (M P Schon et al., Psoriasis, New Engl J Med, 352:1899-1912, 2005). Unraveling the pathogenesis of psoriasis shows that several proangiogenic mediators are activated and highly expressed during psoriasis (R Heidenrich et al., Angiogenesis: the new potential target for the therapy of psoriasis? Drug News Perspect, 21(2):97-105, 2008). Vascular endothelial growth factor, hypoxia-inducible factor, tumor necrosis factor, interleukin-8 and angiopoietins are considered to be the main players responsible for the strong vessel formation in psoriasis. The proangiogenic milieu in the skin seems to result from a proinflammatory immune response initiated by T helper cells. Psoriasis is characterized by the formation of sharply demarked erythematous plaques with large scaling. Plaque formation occurs mainly at sites of strong mechanical stress such as the sites of stretched skin. Elbows, knees and scalp are involved in the majority of patients. Most patients with moderate to severe psoriasis require long-term systemic treatment to control their psoriasis.

In addition to markers of immune activation, markers of oxidative stress are consistently elevated in psoriasis patients and coupled with antioxidant dysfunction. These patients have increased carbonylation (oxidative stress marker) of macromolecules in skin biopsies and cultured fibroblasts, increased plasma malondialdehyde (lipid peroxidation product), increased urine 8-hydroxydeoxyguanosine (a marker of DNA oxidation) and nitrate (a product of nitric oxide), increased lipid hydroperoxides, and lower serum antioxidants (A J Gill and D L Kolson, Dimethyl fumarate modulation of immune and antioxidant responses: application to HIV therapy, Crit Rev Immunol, 33(4):307-59, 2013; references cited therein)

Psoriasis is also characterized by an impaired skin barrier (U Huffmeier, H Traupe, V Oji et al., Loss-of-function variants of the filaggrin gene are not major susceptibility factors for psoriasis vulgaris or psoriatic arthritis in German patients, J Invest Dermatol, 127:1367-1370, 2006). It has been reported that <5% of patients with psoriasis have filaggrin (FLG) mutations and 80% of psoriasis patients have FLG deficiency in their skin (U Huffmeier eta al, J Invest Dermatol, 127:1367-370, 2006). Kim et al have shown that the deficiency FLG and Loricrin (LOR) in most patients with psoriasis is due to TNF-α activation (B E Kim, M D Howell, E Guttman et al, TNF-α down regulates filaggrin and loricrin through c-Jun N-terminal kinase: Role for TNF-α antagonists to improve skin barrier, J Invest Dermatol, 13:1272-1279, 2011).

In summary, psoriasis is a chronic inflammatory skin diseases involving numerous immune axes, particularly various arms of the T-lymphocyte axis; elevated oxidative stress; impaired antioxidant responses and barrier dysfunction.

Fumaric acid occurs naturally and is an important compound biochemically since it enters into the citric acid cycle. Fumarate is a by-product at certain stages in the arginine-urea cycle and in purine biosynthesis. Since the citric acid cycle is the center for energy production, fumaric acid must be present in every cell of the body as it is a by-product of the cycle. Fumaric acid is metabolically very active. In healthy individuals, fumaric acid is formed in the skin when it is exposed to sunlight. Apparently, patients suffering from psoriasis have a biochemical defect in which they can't produce enough fumaric acid and need prolonged exposure to the sun to produce it. This is why patients frequently notice an improvement of their skin condition in the summer months and also explains, in part, the efficacy of PUVA treatment.

Fumaric acid esters (FAE) have been used for well over 25 years in the treatment of psoriasis in Europe under the trade name Fumaderm (formulation of dimethyl fumarate and ethylhydrogen fumarate) (U Mrowietz and K Asadullah, Dimethylfumarate for psoriasis: more than a dietary curiosity, Trends Mol Med, 11:43-48, 2005). 50 to about 70% psoriasis patients show clinical improvement of at least 75% after about four months treatment (D Pathirana et al., European S3-guidelines on the systemic treatment of psoriasis vulgaris, J Eur Acad Dermatol Venereol, 23 suppl 2:1-70, 2009). This treatment response is comparable to the efficacy of first generation anti-TNF-α biologics, but at a much lower cost. Long-term treatment with FAE shows favorable safety profile (J J Hoefnagel et al., Long-term safety aspects of systemic therapy with fumaric acid esters in severe psoriasis, Brit J Dermaol, 149:363-369, 2003; K Reich et al., Efficacy and safety of fumaric acid esters in the long-term treatment of psoriasis—a retrospective study (Future), J Dtch Dermatol Ges, 7:603-611, 2009).

Dimethyl fumarate (DMF) and its primary metabolite monomethyl fumarate (MMF) have been shown to increase expression of anti-inflammatory cytokines interleukin IL-10, IL-4, and IL-6 while inhibiting expression of proinflammatory cytokines IL-6, IL-1 beta, and tumor necrosis factor alpha (K Asadullah et al. Influence of monomethylfumarate on monocytic cytokine formation—Explanation for adverse and therapeutic effects in psoriasis? Arch Dermatol Res, 289:623-630, 1997; R de Jong et al., et al. Selective stimulation of T helper 2 cytokine response by the anti-psoriasis agent monomethylfumarate, Eur J Immunol, 26:2067-2074, 1996; S Schilling et al., Fumaric acid esters are effective in chronic experimental autoimmune encephalomyelitis and suppress macrophage infiltration, Clin Exp Immunol, 145:101-107, 2006). MMF has also been shown to increase, on a dose-dependent basis, transglutaminase (TGase) activity, a marker of late keratinocyte differentiation, as well as keratin 10 (K10), a marker of early keratinocyte differentiation (I A Helwa et al., The mechanism of monomethyl fumarate (MMF) as an anti psoriatic agent, J Invest Dermatol, 132:S51-S64, 2012).

A study on gene expression profiling on RNA derived from psoriatic plaque biopsies taken before and after 12 weeks of FAE treatment was recently published (A J Onderdijk et al., Regulated genes in psoriasis skin during treatment with fumaric acid esters, Brit J Dermatol, 2014). This study shows that response-to-treatment related FAE specific molecules are the transcription factors PTTG1, NR3C1, GATA3 and NG-kappaBIZ, which are important in normal cutaneous development and disease-inducing Th2 and Th17 pathways.

It is reported that after oral administration, dimethyl fumarate is rapidly cleaved into monomethyl fumarate via esterases in the small intestine (D Werdenberg et al., Presystemic metabolism and intestinal absorption of antipsoriatic fumaric acid esters, Biopharm Drug Dispos, 24:259-273, 2003). Dimethyl fumarate and the primary metabolite monomethyl fumarate have half-lives of 12 minutes and 36 hours, respectively. Peak concentrations of monomethyl fumarate are achieved within 5 to 6 hours. Although the parent compound, dimethyl fumarate, does not display protein binding, monomethyl fumarate is found to be approximately 50% bound (U Mrowietz et al., Treatment of severe psoriasis with fumaric acid esters: Scientific background and guidelines for therapeutic use. The German Fumaric Acid Ester Consensus Conference, Br J Dermatol, 141:424-429, 1999).

Metabolism of monomethyl fumarate is through the citric acid cycle leading to excretion through respiration with no known metabolism by the cytochrome P450 system (D Werdenberg et al., Presystemic metabolism and intestinal absorption of antipsoriatic fumaric acid esters, Biopharm Drug Dispos, 24:259-273, 2003; NH Litjens et al., Pharmacokinetics of oral fumarates in healthy subjects, Br J Clin Pharmacol, 58:429-432, 2004). Administration of a single fumarate tablet (containing dimethyl fumarate and calcium monoethyl fumarate) with food led to variability in serum monomethyl fumarate concentrations, suggesting that dimethyl fumarate should be taken before meals (NH Litjens et al., Pharmacokinetics of oral fumarates in healthy subjects, Br J Clin Pharmacol, 2004; 58:429-432). A more recent study focusing on the metabolites of FAE in human urine revealed what is believed to be the true mode of action of FAE and explained the discrepancy between the fact that DMF is active in-vitro and yet lacking or of low plasma level in-vivo. (M Rostami-Yazdi et al., etection of metabolites of fumaric acid esters in human urine: Implications for their mode of action, J Invest Dermatol, 129:231-24, 2009 and references cited therein). In this regard, it is known that T cells promote inflammatory events in psoriatic skin, and treatment with FAE leads to a reduction of T cells in-vivo, which is in part due to apoptosis before the clinical effect becomes evident. This effect can be explained by DMF's ability to strongly deplete intracellular glutathione which correlates well with induction of apoptosis. Another effect of FAE therapy is that peripheral blood mononuclear cells of psoriasis patients produce lower levels of pro-inflammatory Th-1 cytokines. This study reveals that a considerable part of DMF is not hydrolyzed after oral intake but enters circulation and reacts with glutathione in-vivo. In summary, the postulated mode of action of FAE is based on the ability of DMF to deplete intracellular glutathione in immune cells followed by the generation of anti-inflammatory cytokines and/or induction of apoptosis.

In-vitro studies have shown that DMF and its primary metabolite MMF induce expression of NrF2/NQO1 pathway in endothelial cells (K Benardais, R Pul, V Singh et al., Effects of fumaric acid esters on blood-brain barrier tight junction proteins, Neurosci Lett, 555:165-170, 2013). It has been found that the NrF2 pathway can be regulated by FAE in neurons and that the neuroprotective effects of fumarates are dependent on NrF2-mediated anti-oxidative pathways (R A Linker, D H Lee, S Ryan et al., Fumaric acid ester exert neuroprotective effects in neuroinflammation via activation of the NrF2 antioxidant pathway, Brain, 134:678-692, 2011). Recent human studies by Onderdijk et al. convincingly shown that the NrF2 pathway was differentially expressed in FAE responders as well as non-responders, but not in etanercept treated patients, which suggests an FAE specific effect (A J Onderdijk, D M W Balak, E M Baerveldt et al., Regulated genes in psoriasis in skin during treatment with fumaric acid esters, Brit J Dermatol, 171(4):732-741, 2014).

Furthermore, FAE specific induced pathways in the skin include activation of NrF2 and glutathione pathways (A J Onderdijk, D M W Balak, E M Baerveldt et al., Regulated genes in psoriasis in skin during treatment with fumaric acid esters, Brit J Dermatol, 171(4):732-741, 2014).

In following with and in addition to the foregoing teachings, FAEs and other fumaric acid derivatives have been proposed in the patent literature for use in treating a wide-range of diseases and conditions. A few examples are given below:

- Immunological, autoimmune, and/or inflammatory processes including psoriasis
  - U.S. Pat. No. 6,277,882: Joshi et. al.—Utilization of alkyl hydrogen fumarates for treating psoriasis, psoriatic arthritis, neurodermatitis and regional enteritis
  - US2010144651: Nilsson et. al.—Novel glucopyranose esters and glucofuranose esters of alkyl-fumarates and their pharmaceutical use
- Asthma and chronic obstructive pulmonary diseases
  - US 2007/0027076: Joshi et. al.—Use of fumaric acid derivatives for treating cardiac insufficiency, and asthma
- Cardiac insufficiency including left ventricular insufficiency, myocardial infarction and angina pectoris
  - US 2007/0027076: Joshi et. al.—Use of fumaric acid derivatives for treating cardiac insufficiency, and asthma
- Mitochondrial and neurodegenerative diseases such as Parkinson's disease, Alzheimer's disease, Huntington's disease, retinopathia pigmentosa and mitochondrial encephalomyopathy
  - US 2006/0205659: Joshi et. al.—Fumaric Acid Amides
  - U.S. Pat. No. 6,509,376: Joshi et. al.—Utilization of dialkyfumarates
  - U.S. Pat. No. 6,858,750: Joshi et. al.—Use of fumaric acid derivatives for treating mitochondrial diseases
  - U.S. Pat. No. 7,157,423: Joshi et. al.—Fumaric acid amides
- Transplantation
  - US 2006/0205659: Joshi et. al.—Fumaric Acid Amides
  - U.S. Pat. No. 6,359,003: Joshi et. al.—Use of fumaric acid derivatives in transplant medicine
  - U.S. Pat. No. 6,509,376: Joshi et. al.—Utilization of dialkyfumarates
  - U.S. Pat. No. 7,157,423: Joshi et. al.—Fumaric acid amides US 2014/066505: Joshi et. al.—Utilization of Dialkylfumarates Autoimmune diseases including multiple sclerosis (MS)

U.S. Pat. No. 6,509,376: Joshi et. al.—Utilization of dialkyfumarates

U.S. Pat. No. 7,157,423: Joshi et. al.—Strebel, Fumaric acid amides

US 2006/0205659: Joshi et. al.—Strebel, Fumaric Acid Amides

U.S. Pat. No. 6,436,992 and U.S. Pat. No. 7,320,999: Joshi et. al.—Use of fumaric acid derivatives US 2008/0089896: Wang et al.—Bivalent SMAC mimetics and the uses thereof U.S. Pat. No. 8,399,514: Lukashev et. al.—Treatment of multiple sclerosis U.S. Pat. No. 8,669,281 B1: Zeidan et. al.—Prodrugs of fumarates and their use in treating various diseases U.S. Pat. No. 8,759,393, U.S. Pat. No. 8,524,773, U.S. Pat. No. 7,915,310, U.S. Pat. No. 7,803,840, U.S. Pat. No. 7,619,001, and U.S. Pat. No. 7,612,110: Joshi et al.—Utilization of dialkylfumarates Ischemia and reperfusion injury US 2007/0027076: Joshi et. al.—Use of fumaric acid derivatives for treating cardiac insufficiency, and asthma.

Despite their attributes, as noted above, fumarates are associated with many drawbacks. For example, therapy with fumarates products like Fumaderm frequently gives rise to flushing and/or gastro-intestinal side effects such as bloating, fullness, diarrhea, upper abdominal cramps, flatulence and nausea (Gold et al., New. Eng. J. Med., 367(12):1098-1107, 2012). Additionally, DMF and MMF are known skin sensitizers (Lammintausta et al., Contact Dermatitis, 62(2): 88-96, 2010) and, therefore, present serious issues in terms of product handling. Furthermore, topical application is completely precluded and, in any event, DMF is ineffective when administered topically.

Problems are compounded by the fact that present commercially available products generally contain a combination of at least two different fumarate esters, one of which (the monomethyl ester) is present in three different forms: the calcium salt, the magnesium salt and the zinc salt). Although each individual form may have its own therapeutic profile it would be advantageous to have a much simpler and well defined product, if possible, in order to obtain a suitable therapeutic effect.

An alternative approach and the principal current trend of research for anti-psoriasis drugs is towards biologicals—a novel but costly type of therapy having many serious side effects. For example, these medications can predispose patients to infections and increase their risk of developing various malignancies. From a public health standpoint, the development of active tuberculosis in some patients with these biologicals is a matter of serious concern. Similarly, there has been found an increased risk for a variety of malignant conditions such as lymphoma, leukemia and melanomas. (Review: R K Sivamani, G Correa, Y Ono, M P Bowen, S P Raychaudhuri, E Maverakis, Biological Therapy of psoriasis, Indian J Dermatol, 55(2):161-170, 2010).

Accordingly, there is a need to develop novel therapeutically and/or prophylactically active compounds that provide an alternative to existing medicaments, especially the current commercial fumaric acid esters, and biologicals for psoriasis and other diseases. In particular, there is a need for new and/or improved oral and/or topical treatments, especially those that manifest a reduction in flushing and/or gastro-intestinal related side effects along with, most especially, particularly with respect to the latter, an increased bioavailability as well as treatments that are devoid of skin sensitization when applied topically.

SUMMARY OF THE INVENTION

In accordance with the present disclosure there are provided novel products which ameliorate, reduce and/or reverse the effects and/or manifestation of psoriasis as well as other disease conditions that share common gene expression profiles. Specifically, it has now been found that isosorbide di-(methylfumarate) (IDMF) and/or isosorbide mono (methyfumarate) (IMMF) having the general formula (I):

(I)

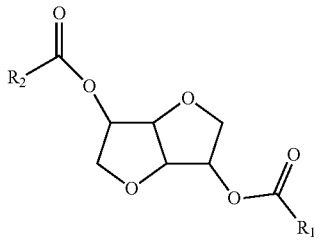

in which $R_1$ and $R_2$ are both —CH═CH—COOMe or one of $R_1$ and $R_2$ are H and the other —CH═CH—COOMe are very effective in the treatment of psoriasis and other disease conditions that share common gene expressions. IDMF and IMMF have been found to be multi-targeted/targeting compounds which simultaneously affect various factors/conditions of the disease for which they administered. Though not intended to be bound by theory, it is believed that these compounds act through various potent anti-inflammatory and antioxidant pathways. Additionally, IDMF is devoid of skin sensitization and flushing. Furthermore, these compounds may be formulated with or into various known carriers and/or treatment compositions and may be administered by any of the known or yet to be discovered pharmaceutical methods of applications, e.g., oral, topical, intramuscular, intravenous, transdermal, as well as sustained/timed release dosing.

While these compounds are effective individually, they may be used in combination with each other, e.g., combinations of two or more compounds meeting Formula I above, or in combination with other pharmacologically active compounds, particularly compounds that similarly reduce, ameliorate, inhibit or otherwise address or treat symptoms and/or conditions associated with the diseases to be addressed by the compounds of the present teaching. Most especially, the present teaching is directed to combinations of one or more of the compounds of Formula I with one or more compounds of Formula II and/or Formula III:

(II)

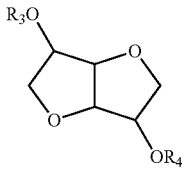

-continued (III)

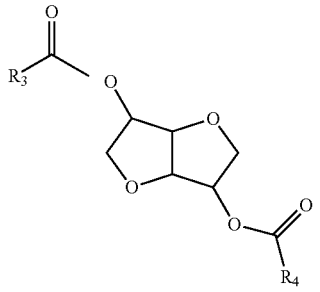

wherein $R_3$ and $R_4$, which may be the same or different, are independently selected from straight chain or branched; saturated or unsaturated alkyl groups having from 4 to 30 carbon atoms, preferably from 6 to 22 carbon atoms, most preferably from 8 to 18 carbon, said carbon number including the carbonyl carbon atom in the case of structure (II), provided that when $R_3$ and $R_4$ are different, one of $R_3$ or $R_4$ may also be hydrogen or a straight chain or branched; saturated or unsaturated alkyl group of from 1 to 4, preferably 1 to 3, carbon atoms. Especially preferred compounds of Formula III include those wherein $R_3$ and $R_4$ are both C17 species, namely the di linoleate esters (two unsaturation), the di-oleate esters (one unsaturation) and/or the di-stearate esters (no unsaturation); both C15 species, namely, the di-palmitate esters no unsaturation); or the C8 species, namely the di-caprylate esters, or combinations of two or more of the foregoing. Among other benefits, these isosorbide esters are selected to be included in topical formulations for alleviating dry skin, a common problem of psoriatic patients.

DETAILED DESCRIPTION OF THE INVENTION

Figures 1A, 1B:
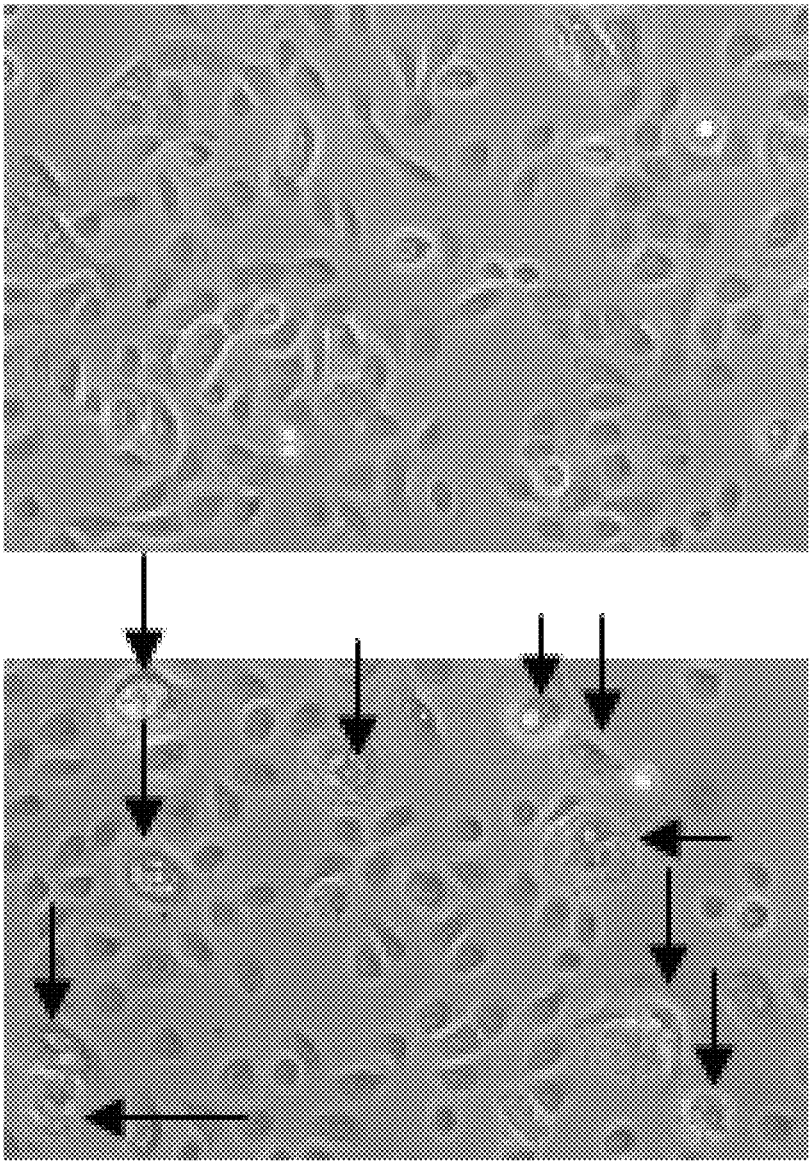
FIGS. 1A and 1B are photomicrographs showing the morphology of human epidermal keratinocyte progenitors not treated (FIG. 1A) and treated with IL-17A/IL-22/TN-α for 48 hours (FIG. 1B).

As used in the present specification, the following terms shall have the meanings as presented:

"Patient" refers to a mammal, for example, a human.

"Pharmaceutically acceptable" means that the subject of this descriptor has been approved or is otherwise approvable by a regulatory agency of a government or governmental or is listed in the U.S. Pharmacopoeia or other generally recognized pharmacopoeia for use in animals, and more particularly in humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient, which does not destroy or have a marked adverse effect on the pharmacological activity of the therein contained pharmacological active agent or metabolite thereof and which is non-toxic when administered in doses sufficient to provide a therapeutically effective amount of the pharmacological active agent or metabolite thereof "Pharmaceutical composition" refers to a composition comprising a pharmaceutically acceptable vehicle and a pharmacological active agent or metabolite, especially, in the case of Pharmaceutical compositions claimed by the present application, pharmacological actives of Formula (I).

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease orreducing the risk of developing a disease or at least one of the clinical symptoms of a disease. "Treating" or "treatment" also refers to inhibiting a disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of a disease or at least one or more symptoms thereof in a patient who may be exposed to or predisposed to a disease even though that patient does not yet experience or display symptoms of the disease.

"Improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

"Inhibiting" generally refers to prevention of the onset of the symptoms, alleviating the symptoms, or eliminating the disease, condition or disorder.

"Optional" or "optionally" means that the subsequently described subject, event or circumstance may or may not occur, and that the description includes instances where the event occurs and instances where it does not and/or when the subject is present and when it is not present.

"Therapeutically effective amount" refers to the amount of a compound that, when administered to a patient for treating a disease, or at least one of the clinical symptoms of a disease, is sufficient to effect such treatment of the disease or symptom thereof. The "therapeutically effective amount" may vary depending, for example, on the compound, the disease and/or symptoms of the disease, severity of the disease and/or symptoms of the disease, the age, weight, and/or health of the patient to be treated, and the judgment of the prescribing physician. An appropriate amount in any given compound may be ascertained by those skilled in the art and/or is capable of determination by routine experimentation.

"Therapeutically effective dose" refers to a dose that provides effective treatment of a disease in a patient. A therapeutically effective dose may vary from compound to compound and/or from patient to patient, and may depend upon factors such as the condition of the patient and the route of delivery as well as those described in the preceding definition of therapeutically effective amount. A therapeutically effective dose may be determined in accordance with routine pharmacological procedures known to those skilled in the art.

Erring on the side of caution and in an effort to avoid having overlooked or inadvertently omitted certain descriptive matter, particularly complementary and supplementary descriptive matter, it is hereby stated and affirmed that the technical publications as well as the patent and patent application publications mentioned herein are all incorporated herein in their entirety by this reference. Indeed, for example, while the current specification could present page after page of description of suitable pharmaceutically acceptable vehicles, such would not be productive as the same are well known and well recognized by those skilled in the art and those that come into being subsequent to the filing of this application will readily be appreciated as suitable as well. The same holds true for many other potential constituents, both active and non-active, that may be employed in pharmaceutical compositions made in accordance with the present teachings.

In accordance with a first aspect of the present disclosure there are provided novel compounds according to the general formula (I):

(I)

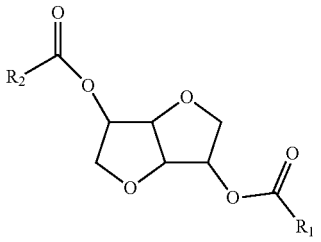

in which $R_1$ and $R_2$ are both —CH═CH—COOMe or one of $R_1$ and $R_2$ are H and the other —CH═CH—COOMe (Me is methyl) which compounds are herein referred to as isosorbide di-(methylfumarate) ("IDMF") ($R_1$=$R_2$) and isosorbide mono-(methyfumarate) ("IMMF") ($R_1 \neq R_2$). It is to be appreciated that in the above formula (I), the structural orientation of the —$OCOR_1$ and —$OCOR_2$ groups may be in an endo orientation (an isomannide), an exo orientation (an isoidide) or one may be endo and the other exo (an isosorbide). Owing to their structure, the isomannide and isoidide compounds are both symmetrical molecules; whereas, because isosorbide has one endo and one exo group, mono-acylation gives rise to two different non-equivalent ester products, namely a 2-ester or a 5-ester. Generally speaking, these compounds have the characteristics of bis secondary alcohols attached to two cis-fused tetrahydrofuran rings and as such possess the properties of both diols and ethers. The preferred compound of formula (I) is the isosorbide di-(methyl fumarate) (IDMF) whose structure (IV) is given below:

(IV)

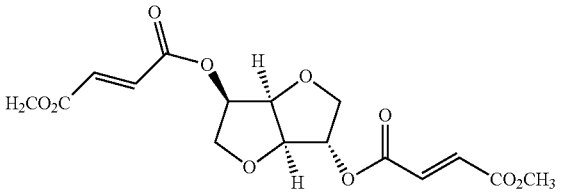

The compounds of formula (I) above are derived from dianhydrohexitols which are well documented by-products of the starch industry obtained by dehydration of D-hexitols, which are made by a simple reduction of hexose sugars. About 650,000 tons of dianhydrohexitols are produced annually worldwide. These chiral biomass-derived products exist as three main isomers (isosorbide (V), isomannide (VI), and isoidide (VII)), depending on the configuration of the two hydroxyl functions (derived from D-glucose, D-mannose, and L-fructose, respectively). Isosorbide, which is produced from glucose via sorbitol, is the most widely available dianhydrohexitol.

V

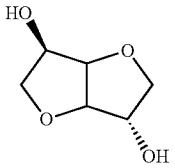

Isosorbide

VI

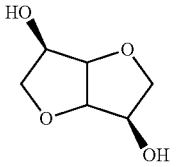

Isomannide

VII

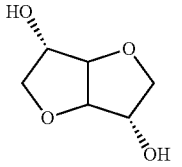

Isoidide

These compounds, as well as the lower ($C_1$-$C_4$) mono- and di-alkyl ethers thereof, and the mono and di-nitrates thereof, are well known and already used in various medical, pharmaceutical and health and beauty applications. The unsubstituted and lower alkyl substituted isohexides are very soluble in water and biologically harmless. The lower alkyl ethers and the unsubstituted compounds have been used as carriers in a number of skin care products to aid in the transport of other active ingredients through the skin membrane. The lower alkyl ethers have also found utility in dentifrices, aiding in the removal of plaque due to their osmotic properties. Isosorbide dinitrate and isosorbide mononitrate have been used to treat angina pectoris. Like other nitric oxide donors, these drugs lower portal pressure by vasodilation and decreasing cardiac output.

The IDMF and IMMF compounds according to the present disclosure may be formed by any of the known methods for the alkanoyl substitution of isohexides or by modified versions of those methods, as will be apparent to those skilled in the art having the benefit of this disclosure. Esterification is among the simplest and most often performed organic transformations. The most common esterification processes involve nucleophilic acyl substitution where the carbonyl compound is used as an electrophile and is attacked by a nucleophilic alcohol, such as the isohexides in the present disclosure. However, other processes are possible; for example, esterification by alkylation reverses the roles of "classic" carbonyl chemistry: a carboxylate anion is used as a nucleophile that displaces a halide ion in an SN2 reaction.

In following, in accordance with a second aspect of the present teaching there is provided a process for producing the compounds of formula (I). This involves esterifying isosorbide (V)

V

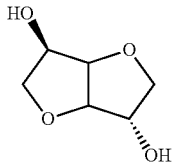

a) with about 2 to 3 moles of methyfumarate to form the diester or
b) with about 2 to 3 moles of methyfumarate to form the diester and then hydrolyzed in a controlled manner to form the monoester, or
c) with 1 mole of methylfumarate to form the monoester, or
d) with 2 to 3 moles of fumaric acid to form the diester, or
e) with 2 to 3 moles of fumaric acid to form the diester and then hydrolyzed in a controlled manner to form the monoester, or
f) with 1 mole of fumaric acid to form the monoester.

Following production of the final mono- or di-ester, the reaction product is then preferably purified to remove, if present, excess reactants, contaminants, by-products and other undesirable materials.

In accordance with a third aspect of the present teachings, the compounds of the present teachings have, surprisingly, been found to be very effective in the treatment of psoriasis and other disease conditions that share common gene expressions. In this respect, IDMF and IMMF have been found to be multi-targeted/targeting compounds which simultaneously affect various factors/conditions of the disease for which they administered. Though not intended to be bound by theory, it is believed that these compounds act through various potent anti-inflammatory and antioxidant pathways. Additionally, IDMF is devoid of skin sensitization and flushing. Furthermore, these compounds may be formulated with or into various known pharmaceutically acceptable vehicles and/or pharmaceutical compositions and may be administered by any of the known or yet to be discovered pharmaceutical/treatment. Indeed, depending upon the targeted disease and/or condition, the compounds of the present teaching may be administered in accordance with various methods of application, e.g., oral, topical, intramuscular, intravenous, transdermal, and formulation, as the sole active or as one of several actives, which may act independently or in conjunction with one another as well as in formulations that allow for sustained/timed release dosing.

As noted above, the compounds of formula [(i)] *I*, especially the dianhydrohexitol di-(methylfumarate)s, most especially Isosorbide di-(methylfumarate) (IDMF), has surprisingly been found to provide a marked effect in ameliorating, reducing and/or reversing or otherwise treating the effects and/or manifestation of psoriasis as well as other disease manifesting similar symptoms and/or sharing common gene expression profiles, at least with respect to those genes that appear to be disease related. While not intending to be bound by theory or mechanisms, it is believed that these compounds, especially IDMF, is capable of modulating key genes/proteins responsible for chronic inflammation in psoriasis involving numerous immune axes, particularly various arms of the T-lymphocyte axis, and elevated oxidative stress, impaired antioxidant responses and barrier dysfunction.

While these compounds are effective individually, the compounds of the present teaching may be, and are preferably and/or beneficially, used in combination with each other, e.g., combinations of two or more compounds meeting Formula (I) above, and/or in combination with other pharmacologically active compounds, particularly compounds that similarly reduce, ameliorate, inhibit or otherwise address or treat symptoms and/or conditions associated with the diseases to be addressed by the compounds of the present teaching. Such combinations of compounds and actives provide further surprising results in terms of their pharmacological activity, especially with respect to the treatment of psoriasis and other diseases which manifest and/or have common effects on gene expression profiles. Such other pharmaceutical actives may be selected to treat the same disease or symptoms as the compounds of formula (I) or a different disease or symptom. Alternate drugs useful for treating psoriasis which may be combined with the compounds of formula (I) or into which compounds of Formula (I) may be incorporated include, but are not limited to, etanercept, adalimumab, triamcinolone, cortisone, infliximab, golimumab, di- or mono-alkyl fumarates, and retinoids. Most especially, as noted above, the compounds of formula (I) are used in combination with compounds of Formulae II and III, may be, and preferably are, incorporated into various pharmaceutical compositions for administration to a patient. These additional actives may be combined together and the combination of actives administered as a single pharmaceutical composition or administered independently, in concurrent or sequentially administered pharmaceutical compositions.

Thus, in accordance with yet another aspect of the teaching of the present disclosure there are provided pharmaceutical compositions and methods of treatment comprising a combination of two or more compounds according to formula (I) above as well as combinations of at least one compound of formula (I) above and one or more other suitable pharmaceutical active. Such combinations of active compounds and their application or administration is found to have improved and/or synergistic performance, particularly with respect to the treatment of psoriasis and diseases which manifest similar symptoms and/or common gene expression profiles. For example, one preferred class of other pharmaceutical actives is those compounds that are capable of activating granular-layer activating genes, more specifically, skin aspartic proteases (SASPase) and filaggrin. In this regard, it has been reported that <5% of patients with psoriasis have filaggrin (FLG) mutations and 80% of psoriasis patients have FLG deficiency in their skin (U Huffmeier et al, J Invest Dermatol, 127:1367-370, 2006). Research demonstrates that SASPase activity is indispensable for processing profilaggrin and maintaining the texture and hydration of the SC (EMBO Mol Med, 3(6):320-33, 2011). Additionally, Bernard et al have identified SASPase in the granular layer of human epidermis (J Invest Dermatol, 125:156-159m 2005). Thus, the presence of such compounds or actives in the compositions according to the present teaching leads to reinforcement and/or enhancement in the skin barrier function and stimulation of epidermal regeneration and differentiation.

Among the preferred active compounds that may be used in combination with the compounds of formula (I) are those of Formula II and/or Formula III:

(II)

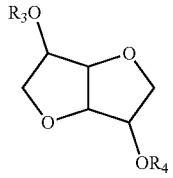

(III)

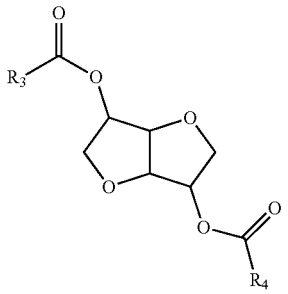

wherein $R_3$ and $R_4$, which may be the same or different, are independently selected from straight chain or branched; saturated or unsaturated alkyl groups having from 4 to 30 carbon atoms, preferably from 6 to 22 carbon atoms, most preferably from 8 to 18 carbon, said carbon number including the carbonyl carbon atom in the case of structure (II), provided that when $R_3$ and $R_4$ are different, one of $R_3$ or $R_4$ may also be hydrogen or a straight chain or branched; saturated or unsaturated alkyl group of from 1 to 4, preferably 1 to 3, carbon atoms. These compounds and their manufacture are disclosed in, e.g., U.S. Pat. No. 8,496,917B2, which is incorporated herein by reference. Like the compounds of the present disclosure, i.e., formula (I), compounds of Formula II and III are based upon reaction products of the dianhydrohexitols V, VI and VII, most notably V, and various long chain halides and/or sulfates and acids and/or esters, respectively. These long chain precursors, especially the acids and, are derived from vegetable oils which typically contain these types of acids as triglycerides. Oftentimes vegetable oils contain 60% or more of the higher acid esters: exemplary sources include Salicornia oil, Safflower oil, Evening primrose oil, poppy seed oil, Grape seed oil. Sunflower oil, Barberry fig seed oil, Hemp oil and Corn oil.

In yet another preferred embodiment of the present teaching preferred pharmaceutical compositions of the present teaching comprise at least one compound of formula (I) in combination with one or more compounds of formula (II) wherein $R_3$ and $R_4$ have from 8 to 18 carbon atoms, more preferably 16 to 18 carbon atoms. Most especially, the compounds of formula II are those wherein $R_3$ and $R_4$ are both C17 species, namely the di-linoleate esters (two unsaturation), the di-oleate esters (one unsaturation) and/or the di-stearate esters (no unsaturation); both C15 species, especially, the di-palmitate esters (no unsaturation); or the C8 species, especially the di-caprylate esters, or combinations of two or more of the foregoing.

Generally speaking, pharmaceutical compositions provided by the present disclosure comprise a therapeutically effective amount of a compound of Formula (I) and one or more pharmaceutically acceptable vehicles. Of course these compositions may include other actives and conventional ingredients of pharmaceutical compositions, all of which are well known in the art. The selection of the pharmaceutically acceptable vehicles as well as other conventional ingredients depends, to a large extent, upon the mode of administration and the symptoms of the disease to be addressed. For example, in the case of topically applied pharmaceutical compositions, these compositions may optionally include an effective amount of one or more skin protective and/or treatment ingredients such as antioxidants, sunscreens, vitamins, anti-inflammatory agents, self-tanning agents, moisturizers, emollients, humectants, compatible solutes and the like, and mixtures thereof, in their conventional amounts. These compositions may also include other ingredients that have no or little bearing upon the intended end-use or application of the pharmaceutical composition, but aid in the preparation thereof, such as solubilizers, surfactants, etc.

Similarly, the final form of the pharmaceutical compositions and their method of manufacture also depend, in part, upon the mode of mode of administration. For example, the pharmaceutical compositions comprising a compound of Formula (I) may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (I), or crystalline forms thereof and one or more pharmaceutically acceptable vehicles into formulations that can be used pharmaceutically. Pharmaceutical compositions provided by the present disclosure may take the form of solutions, suspensions, emulsions, tablets, pills, pellets, capsules, capsules containing liquids, powders, creams, lotions, gels, sustained-release formulations, suppositories, emulsions, aerosols, sprays, suspensions, or any other form suitable for administration to a patient.

The pharmaceutical compositions provided by the present disclosure may be formulated in a unit dosage form. A unit dosage form refers to a physically discrete unit suitable as a unitary dose for patients undergoing treatment, with each unit containing a predetermined quantity of a compound of Formula (I) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

The pharmaceutical compositions comprising a compound of Formula (I) may be formulated for immediate release or for delayed or controlled release. In this latter regard, certain embodiments, e.g., an orally administered product, may be adapted for controlled release. Controlled delivery technologies can improve the absorption of a drug in a particular region, or regions, of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some drugs, maintaining a constant blood and tissue concentration of the drug throughout the course of therapy is the most desirable mode of treatment as immediate release of drugs oftentimes causes blood levels to peak above that level required to elicit a desired response. This results in waste of the drug and/or may cause or exacerbate toxic side effects. In contrast, the controlled delivery of a drug can result in optimum therapy; not only reducing the frequency of dosing, but also reducing the severity of side effects. Examples of controlled release dosage forms include dissolution controlled systems, diffusion controlled systems, ion exchange resins, osmotically controlled systems, erodable matrix systems, pH independent formulations, and gastric retention systems.

As noted, the compounds of formula (I), more appropriately, the pharmaceutical compositions comprising compounds of formula (I), may be administered through any conventional method. The specific mode of application or administration is, in part, dependent upon the form of the pharmaceutical composition, the primary purpose or target of its application (e.g., the application may be oral if intending to address the disease generally or topically if intending to address primarily a topical symptom of the disease. Suitable modes of administration include, for example, intradermal, intramuscular, intraperitoneal, intravenous, subcutaneous, intranasal, epidural, oral, sublingual, intracerebral, intravaginal, transdermal, rectal, inhalation, or topical. Especially preferred modes of administration are oral, topical or those methods that involve absorption through epithelial or mucous linings (e.g., oral mucosa, rectal, and intestinal mucosa, etc.). Furthermore, again, depending in part upon the form and primary purpose or target of the administration, the pharmaceutical compositions of the present disclosure may be administered systemically or locally. Finally, the form of the pharmaceutical composition and its delivery system may also vary depending upon the parameters already noted. For example, orally administered pharmaceutical compositions of the present teaching may be in encapsulated form, e.g., encapsulated in liposomes, or as microparticles, microcapsules, capsules, etc. Similarly, topically applied pharmaceutical compositions of the present teachings may be applied as a liquid, cream, gel, spray, lotion, etc.

Again as noted above, the compounds of formula (I) may be used as is, i.e., as 100% of the composition to be applied; however, the compounds of formula (I) are preferably incorporated into a pharmaceutical composition in which the compound(s) of formula account for from about 0.01 to about 99 weight percent of the pharmaceutical composition. Preferably, the compounds of formula (I) will comprise from about 0.5 to about 30 wt %, more preferably from about 0.5 to about 20 wt %, most preferably from about 1.0 to about 10 wt % of the pharmaceutical composition. Another factor playing into the concentration of the compounds of formula (I) in the pharmaceutical composition is the dose or rate of application of the compounds to the patient. Obviously, dosing itself depends upon a number of factors including the concentration and/or purity of the compounds of formula (I), the efficacy thereof, the individual to whom the pharmaceutical is to be administered, the mode of administration, the form in which the pharmaceutical composition is to be administered, the disease or symptom to be addressed, etc.

The foregoing factors as well as the application thereof in formulating the compositions of the present teaching are all as well known in the art whereby the final or actual concentration in the pharmaceutical composition and/or the dose can readily be determined based up simple dose-response testing and the like. For example, an appropriate oral dosage for a particular pharmaceutical composition containing one or more compounds of formula (I) will depend, at least in part, on the gastrointestinal absorption properties of the compound, the stability of the compound in the gastrointestinal tract, the pharmacokinetics of the compound and the intended therapeutic profile. An appropriate controlled release oral dosage and ultimate form of a pharmaceutical composition containing a particular compound of Formula (I) will also depend upon a number of factors. For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Again, it is to be expected that certain compounds may be absorbed primarily from the small intestine whereas others are absorbed primarily through the large intestine. It is also to be appreciated that while it is generally accepted that compounds traverse the length of the small intestine in about 3 to 5 hours, there are compounds that are not easily absorbed by the small intestine or that do not dissolve readily. Thus, in these instances, the window for active agent absorption in the small intestine may be too short to provide a desired therapeutic effect in which case large intestinal absorption must be channeled and/or alternate routes of administration pursued.

Generally speaking, an appropriate dose of a compound of Formula (I), or pharmaceutical composition comprising a compound of Formula (I), may be determined according to any one of several well-established protocols including in-vitro and/or in-vivo assays and/or model studies as well as clinical trials. For example, animal studies involving mice, rats, dogs, and/or monkeys may be used to determine an appropriate dose of a pharmaceutical compound. Results from animal studies may be and typically are extrapolated to determine appropriate doses for use in other species, such as for example, humans.

As noted above, the compositions according to the present teaching may be designed for immediate infusion or application of the actives to the body or site of the symptom to be treated. However, it is also recognized that in certain instances the pharmaceutical compositions provided by the present disclosure may be, and are preferably, adapted to provide sustained or timed release of a compound of Formula (I): this is especially so and desirable for oral administration. Sustained release oral dosage forms are used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

Following on the foregoing, the amount of a compound of Formula (I) contained in a dose may depend on the route of administration and whether the disease in a patient is effectively treated by acute, chronic, or a combination of acute and chronic administration. In any event, the administered dose is typically less than a toxic dose: though it may have significant adverse health effects, provided that the desired beneficial effect is also attained. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a compound or metabolite thereof may exhibit a high therapeutic index. The data obtained from these cell culture assays and animal studies may be used in formulating a dosage range that is not toxic for use in humans. A dose of a compound of Formula (I) may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Where additional pharmaceutical actives are also present in the compositions according to the present teaching, the amount by which they are present and/or the dosage amount will typically be consistent with their conventional concentration and rates of application. For example, the compounds of formulae II and III will be present in an amount of from about 0.5 to about 30 wt %, more preferably from about 0.5 to about 20 wt %, most preferably from about 1.0 to about 10 wt % of the pharmaceutical composition. Of course, as noted, the combination of pharmaceutical actives with the compounds of formula (I) also provide enhanced performance and/or synergy whereby the amounts of each and/or the dose of each may be and is generally less than required for the use of the active compounds on their own.

Having described inventive compounds, process of making compounds, compositions, and treatment methods in general terms, attention is now directed to the following examples in which specific formulations and applications thereof are evaluated. In the foregoing and in the following examples, unless otherwise indicated, all temperatures are set forth in degrees Celsius and all parts and percentages are by weight. The disclosed embodiments are not intended to be limiting of the claims. To the contrary, the claims are intended to cover all alternatives, modifications, and equivalents.

EXPERIMENTAL

Example 1

Synthesis of Isosorbide Di-(Methylfumarate)

To a suspension of isosorbide (50 g, 0.34 mol) in ethyl acetate (500 ml) was added monomethyl fumarate (97.5 g, 0.75 mol) followed by 4-dimethylaminopyridine (DMAP) (8.3 g, 0.06 mol). The reaction mixture was cooled to 0° C. (ice bath) and a solution of dicyclohexylcarbodiimide (DCC) (168 g, 0.75 mol) in ethyl acetate (800 ml) was added drop wise. The reaction mixture was then allowed to warm up to room temperature and stirred for 16 hrs. Precipitates were filtered and washed with Ethyl acetate (300 ml). The filtrate was concentrated under vacuum to give 176 g crude product. This crude product was shaken in hexane (1 L), filtered and the solid again washed with hexane (500 ml). This resultant solid product was dried and subsequently purified on a short path of silica gel using ethyl acetate/hexane (0 to 50%) to give 87 g of white solid. This solid was recrystallized in hot ethyl acetate (500 ml) to give a total of 60 g of pure isosorbide di-(methylfumarate)("IDMF"), mp 106-108° C., with a purity of about 98.5% as determined by HPLC. Structure of IDMF was established by $^{1}$HNMR and MS analyses.

TABLE 1

Topical formulations of IDMF at 2 and 5% level

| INCI name | Trade Name/Supplier | % w/w | % w/w |
|---|---|---|---|
| Phase A-1 | | | |
| Water (demineralized) | | Qs | Qs |
| Disodium EDTA | | 0.10 | 0.10 |
| Glycerin | Glycerin 99%/Ruger | 2.00 | 2.00 |
| Butylene Glycol | Butylene Glycol/Ruger | 2.00 | 2.00 |
| Phase A-2 | | | |
| Xanthan Gum | Rhodicare S/Rhodia | 0.10 | 0.10 |
| Acrylates/C10-30 Alkyl Acrylate Crosspolymer | Carbopol Ultrez 21/ Lubrizol | 0.25 | 0.25 |
| Phase B | | | |
| Caprylic/Capric Triglycerides | Myritol 318/Cognis | 6.00 | 4.00 |
| Mineral Oil, Lanolin Alcohols | Fancol LAO/Elementis | 2.00 | 2.00 |
| Oleth-10 | Brij-10/Croda | 0.50 | 0.50 |
| Glyceryl Stearate, PEG-100 Stearate | Arlacel 165/Croda | 2.50 | 2.50 |
| Dimethicone | DC, 200/100 CST/Dow Corning | 3.00 | 2.00 |
| Stearic Acid | Stearic Acid, NF/Spectrum | 1.00 | 1.00 |
| Cetyl Alcohol | Crodacol C-70/Croda | 1.50 | 1.50 |
| Phase C | | | |
| Triethanolamine | Triethanolamine 99% | 0.15 | 0.15 |
| Phase D | | | |
| Dimethyl Isosorbide | Arlasolve DMI/Croda | 6.00 | 15.00 |
| IDMF(Isosorbide di-methyl fumarate) | IDMF/Sytheon | 2.00 | 5.00 |
| Phase E | | | |
| Phenoxyethanol, Ethylhexylglycerine | Euxyl 9010/Schulke | 1.00 | 1.00 |
| Total | | 100.00 | 100.00 |

Example 2

Topical Formulations of 2% and 5% IDMF

A topical pharmaceutical composition containing IDMF was prepare using the formula as presented in Table 1. The composition was prepared by preparing compositions A-1 and A-2 and then dispersing composition A-2 in A-1 while stirring and heating to 75° C. to form Phase A. Independently, the Phase B ingredients were combined and then heat to 75° C. Phase B was then added to Phase A with good mixing. Phase C was added to a premixed Phase D and the combination then added to the combined Phase A/B. The mixture was then homogenized at moderate speed while cooling to ~40° C. A preservative was added and the composition stirred until a uniform, homogeneous composition attained. The final composition had a pH of 6.0 and a viscosity of 30,000-40,000 cps (sp 4, 5 rpm).

Example 3

Topical Formulations of 2% IDMF and 2% Isosorbide Dilinoleate

A second topical composition was prepare in accordance with the same procedure as that for the preparation of the topical composition of Example 2 with the exception that a combination of IDMF and isosorbide dilinoleate (formula III) was employed. The formulation of the composition is as presented in Table 2.

Example 4

Anti-Psoriatic Effects of IDMF in Psoriasiform Keratinocyte Cultures

Psoriasiform keratinocyte cultures were established by incubating epidermal keratinocyte progenitors from stratum basae (Zen-Bio, RTP, NC) with IL-17A/IL-22/TNFα (100 μg/ml; 100 μg/ml; 10 μg/ml) for 24 h. These cytokines have been reported to be key triggers in psoriasis (Y Tokura, T Mori, R Hino, Psoriasis and other Th17-mediated skin diseases. J UOEH, 32(4):317-328, 2010; A B Van Belle, M de Heusch, M M Lemaire, E Hendrickx, G Wamier, K Dunussi-Joannopoulos, L A Fouser, J C Renauld, L Dumoutier, IL-22 is required for imiquimod-induced psoriasiform skin inflammation in mice, J Immunol, 188(1):462-469, 2012; A Hänsel, C Günther, J Ingwersen, J Starke, M Schmitz, M Bachmann, M Meurer, E P Rieber, K Schäkel, Human slan (6-sulfo LacNAc) dendritic cells are inflammatory dermal dendritic cells in psoriasis and drive strong TH17/TH1 T-cell responses, J Allergy Clin Immunol, 127 (3):787-794, 2011; Kim J, Krueger J G. The Immunopathogenesis of Psoriasis, Dermatol Clin, 33:13-23, 2015).

TABLE 2

2% IDMF and 2% Isosorbide dilinoleate

| INCI name | Trade Name/Supplier | % w/w |
|---|---|---|
| Phase A | | |
| Water (demineralized) | | Qs |
| Disodium EDTA | | 0.10 |
| Glycerin | Glycerin 99%/Ruger | 2.00 |
| Butylene Glycol | Butylene Glycol/Ruger | 2.00 |
| Phase A-1 | | |
| Xanthan Gum | Rhodicare S/Rhodia | 0.10 |
| Acrylates/C10-30 Alkyl Acrylate Crosspolymer | Carbopol Ultrez 21/ Lubrizol | 0.25 |
| Phase B | | |
| Caprylic/Capric Triglycerides | Myritol 318/Cognis | 4.00 |
| Isosorbide dilinoleate | HydrasSynol IDL/Sytheon | 2.00 |
| Mineral Oil, Lanolin Alcohols | Fancol LAO/Elementis | 2.00 |
| Oleth-10 | Brij-10/Croda | 0.50 |
| Glyceryl Stearate, PEG-100 Stearate | Arlacel 165/Croda | 2.50 |
| Dimethicone | DC, 200/100 CST/Dow Corning | 3.00 |
| Stearic Acid | Stearic Acid, NF/Spectrum | 1.00 |
| Cetyl Alcohol | Crodacol C-70/Croda | 1.50 |
| Phase C | | |
| Triethanolamine | Triethanolamine 99% | 0.15 |
| Phase D | | |
| Dimethyl Isosorbide | Arlasolve DMI/Croda | 6.00 |
| IDMF(Isosorbide di-methyl fumarate) | IDMF/Sytheon | 2.00 |
| Phase E | | |
| Phenoxyethanol, Ethylhexylglycerine | Euxyl 9010/Schulke | 1.00 |
| Total | | 100.00 |

In our keratinocyte system, IL-17A/IL-22/TNFα triggered the modulation of expression of genes, such as DEFB4A (18.9 fold), HPGD (−84.5 fold), CXCL3 (3.3 fold) and IL8 (40.7 fold), known to be implicated in psoriasis (M Simanski, F Rademacher, L Schroder, H M Schumacher, R Glaser, J Harder, IL-17A and IFN-γ synergisticall induce RNase 7 expression via STAT3 in primary keratinocytes, PLoS One, 2013; 8(3):e59531, 2013; O Arican, M Aral, S Sasmaz, P Ciragil, Serum levels of TNF-alpha, IFN-gamma, IL-6, IL-8, IL-12, IL-17, and IL-18 in patients with active psoriasis and correlation with disease severity, Mediators Inflamm, (5):273-279, 2005; K Ikai, Psoriasis and the arachidonic acid cascade, J Dermatol Sci, 21(3):135-146, 1999; K Guilloteau, I Paris, N Pedretti, K Boniface, F Juchaux, V Huguier, G Guillet, F X Bernard, J C Lecron, F Morel, Skin Inflammation Induced by the Synergistic Action of IL-17A, IL-22, Oncostatin M, IL-1{alpha}, and TNF-{alpha} Recapitulates Some Features of Psoriasis, J Immunol, 184(9): 5263-5270, 2010; A B Van Belle, M de Heusch, M M Lemaire, E Hendrickx, G Wamier, K Dunussi-Joannopoulos, L A Fouser, J C Renauld, L Dumoutier, IL022 is required for imiquimod-induced psoriasiform skin inflammation in mice, J Immunol, 188(1)462-469, 2012). IL-17A/IL-22/TNFα also caused psoriasiform morphological alterations in these cells (Compare FIG. 1A—non-cytokine treated to FIG. 1B—cytokine treated). These morphological changes result in senescent "fried egg" cells (see arrows in FIG. 1B) which are reminiscent of the senescence-associated secretory phenotype (SASP).

After 24 h of cytokine treatment, the IDMF test materials were added to cells and further incubation with IL-17A/IL-22/TNFα was pursued for another 24 h. At the end of the experiment total RNA was extracted from keratinocytes and quantified using DNA microarrays. DNA microarray quantification clearly showed a general anti-cytokine effect of IDMF, with significant inhibition of TNFα/IFNγ/IL-17 responses, while the antioxidant pathways, especially those related to glutathione, were upregulated, demonstrating the mechanism of action typical for DMF. In addition, the study demonstrated that a number of genes were down regulated by IDMF. These genes have enrichment for NFκB and STAT1 binding sites in their upstream region, adding more evidence for the TNFα/IFNγ/IL-17-targeting mechanism of IDMF.

Table 3 presents the data pertaining to the psoriasis-relevant biological processes most significantly down-regulated by 1 μg/ml IDMF in psoriasiform keratinocytes, as revealed by DNA microarray approach. Table 4 presents the data pertaining to the psoriasis-relevant biological processes most significantly up-regulated by 1 μg/ml IDMF in psoriasiform keratinocytes, as revealed by DNA microarray approach. Note the down regulation of inflammatory responses, with the emphasis on interferon-γ (complete with its downstream inhibition of ICAM1—see Table 4), and the up-regulation of pathways appears to involve redox homeostasis and glutathione synthesis processes, which are the hallmarks of the DMF mechanism of action.

TABLE 3

Psoriasis-relevant pathways in psoriasiform keratinocytes decreased by IDMF (1 μg/ml)

| GOBPID | p-value | Term |
|---|---|---|
| GO:0002685 | 0.000 | regulation of leukocyte migration |
| GO:0090023 | 0.000 | positive regulation of neutrophil chemotaxis |
| GO:0006955 | 0.000 | immune response |

TABLE 3-continued

| Psoriasis-relevant pathways in psoriasiform keratinocytes decreased by IDMF (1 μg/ml) | | |
|---|---|---|
| GOBPID | p-value | Term |
| GO:0060333 | 0.002 | interferon-gamma-mediated signaling pathway |
| GO:0060337 | 0.002 | type I interferon-mediated signaling pathway |
| GO:0034340 | 0.002 | response to type I interferon |
| GO:2000145 | 0.002 | regulation of cell motility |
| GO:0030335 | 0.004 | positive regulation of cell migration |
| GO:0034341 | 0.005 | response to interferon-gamma |
| GO:0006954 | 0.007 | inflammatory response |
| GO:0071347 | 0.012 | cellular response to interleukin-1 |
| GO:0032680 | 0.017 | regulation of tumor necrosis factor production |
| GO:0071706 | 0.019 | tumor necrosis factor superfamily cytokine production |
| GO:0071345 | 0.019 | cellular response to cytokine stimulus |
| GO:0071356 | 0.024 | cellular response to tumor necrosis factor |
| GO:0002697 | 0.026 | regulation of immune effector process |
| GO:0002684 | 0.028 | positive regulation of immune system process |
| GO:0002285 | 0.029 | lymphocyte activation involved in immune response |
| GO:0001819 | 0.033 | positive regulation of cytokine production |
| GO:0045321 | 0.035 | leukocyte activation |
| GO:0017015 | 0.046 | regulation of TGFβ receptor signaling pathway |

Based on these findings, it appears that genes decreased by IDMF correlate significantly with genes increased in psoriatic cells and skin, which inversely correlate with genes increased by anti-psoriatic drugs in patients, confirming the anti-psoriatic potential of IDMF. For example, using enrichment statistic value based on equation (8) from A A Philippakis publication (A A Philippakis, B W Busser, S S Gisselbrecht, F S He, B Estrada, A M Michelson, M L Bulyk, Expression-guided in silico evaluation of candidate cis regulatory codes for Drosophila muscle founder cells, PLoS Comput, Biol, 2(5): e53, 2006), it was found that genes strongly decreased by IDMF were strongly elevated in cultured keratinocytes following treatment with the combination TNFα/IFNγ (GSE accession number 20297), with TNFα/IL-17A, IFNγ (GSE12109; GSE7216), IL1 (GSE9120) or TNFα (GSE24767; GSE36287; GSE32975). Similar strong correlation (stat.>200, $p<10^{-8}$) was found between genes decreased by IDMF and those increased in psoriatic (GSE6710; GSE9120; GSE36387; GSE11903; GSE30999), carcinoma (GSE2503), actinic keratosis (GSE2503), dermatomyositic (GSE32245) and atopic (GSE5667) vs. normal skin. There was a strong positive correlation between genes induced by the anti-inflammatory IL13 and IDMF (GSE36287; stat. 154, $p<10^{-7}$).

TABLE 4

| Psoriasis-relevant pathways in psoriasiform keratinocytes increased by IDMF (1 μg/ml) | | |
|---|---|---|
| GOBPID | p-value | Term |
| GO:0006693 | 0.000 | prostaglandin metabolic process |
| GO:0045454 | 0.004 | cell redox homeostasis |
| GO:0006749 | 0.005 | glutathione metabolic process |
| GO:0006749 | 0.005 | glutathione metabolic process |
| GO:0072593 | 0.010 | reactive oxygen species metabolic process |
| GO:0042592 | 0.010 | homeostatic process |
| GO:0006750 | 0.012 | glutathione biosynthetic process |
| GO:0006968 | 0.033 | cellular defense response |
| GO:1901687 | 0.033 | glutathione derivative biosynthetic process |
| GO:1901687 | 0.033 | glutathione derivative biosynthetic process |
| GO:0006879 | 0.034 | cellular iron ion homeostasis |
| GO:0002065 | 0.039 | columnar/cuboidal epithelial cell differentiation |
| GO:0050931 | 0.040 | pigment cell differentiation |
| GO:0032755 | 0.043 | positive regulation of interleukin-6 production |

Furthermore, genes decreased by IDMF tend to be strongly decreased in psoriasis lesions of patients treated with etanercept (GSE11903; stat. −204, $p<10^{-5}$), efalizumab (GSE30768; stat. −141; p=0.001) or the anti-IL17A biologic LY2439821 (GSE31652; (stat. −193, $p<10^{-4}$). Overall, there were over 200 significant (stat.>0.05/<−0.05; p<0.05) gene expression correlations in favor of the anti-psoriatic and anti-dermatitis activity of IDMF. It was especially encouraging to see an anti-dermatitis response for a compound derived from a skin-sensitizing parent molecule (notwithstanding the obvious limitations of a keratinocyte culture model). On the downside, IDMF seemed to hinder a defense response pathway, because genes decreased by IDMF also show enrichment for an IRF site in the upstream regions (also ISRE), and these same genes tend to be induced in keratinocytes by the poly(I:C) treatment. Polyinosinic: polycytidylic acid (usually abbreviated poly I:C) is an immunostimulant and is an adjuvant used for antitumor treatment and vaccines because of its prominent effects on CD8 T cells and NK cells. Poly(I:C) binds TLR3 and this interaction is thought to be central for driving cell-mediated immune responses (J Immunology, 181(11):7670-7680, 2008). Interestingly, IDMF has retained at least some of the biocidal effect of DMF, possibly partially compensating for the decrease of the defense response pathway.

Furthermore, as shown in Table 5 IDMF appears to suppress interferon-controlled pathways in psoriasiform keratinocytes by repressing multiple genes (last column) with significant enrichment/overrepresentation of STAT1 and NFKB motifs (first column) in their upstream region (1 kb). Induction of IFN-mediated pathways associated with STAT1 binding sites is a robust signature in psoriatic lesions. Enrichment of motifs was calculated using semiparametric generalized additive logistic models.

TABLE 5

| Effect of IDMF on interferon controlled pathways | | | | | | |
|---|---|---|---|---|---|---|
| Motif | Motif ID | Estimate | SE | Z stat | P value | Predicted STAT1/NFKB targets down-regutated by IDMF |
| NFKB\|GGGRAWTYCC | NF_kappaB_disc1 | 0.90 | 0.29 | 3.14 | 0.0016 | RHCG\|MMP9\|GBP1\|KCTD11\|PLAT\|NFKBIZ\|COBLL1\|IL1R2\|BPGM\|IL36G\|IL23A |
| STAT1\|RGAAANYGAAACT\|MA0137 | J9365 | 1.28 | 0.43 | 3.01 | 0.0026 | DDX60\|MX2\|OAS2 |
| STAT1\|GRAANNGAAAS | STAT_disc3 | 1.21 | 0.31 | 3.95 | 7.77E−05 | IFI44L\|MX2\|DDX60\|SAMD9L\|GBP1\|OAS2 |

TABLE 5-continued

Effect of IDMF on interferon controlled pathways

| Motif | Motif ID | Estimate | SE | Z stat | P value | Predicted STAT1/NFKB targets down-regutated by IDMF |
|---|---|---|---|---|---|---|
| NFKB\|GGGACTTYCCA\|M00208 | M00208 | 1.52 | 0.39 | 3.86 | 0.0000 | LTBP1\|SLCO4A1\|PLAT\|ABCA1\|NFKBIZ\|PDZK1IP1\|IL36G |
| STAT1\|TTTCC\|M00496 | M00496 | 0.050 | 0.03 | 2.01 | 0.0449 | SLC6A14\|IL36G\|IFI44L\|IL36RN\|LNX1\|BPGM\|SPINK6\|DDX60\|OAS2\|IL1R2\|CAPND2\|CD200\|GBP1\|NFKBIZ\|EDN1\|KRT75\|ICAM1\|(. . .) |

Example 5

Anti-Psoriatic Effects in Murine Tail Model of Psoriasis

The mouse tail test is a well-established animal model used for the development of FDA-approved anti-psoriasis drugs. Table 6 summarize the findings following 2 weeks of test material application on the tails, with the readout of improvement in stratum granulosum (StGrm) coverage +/− side effects. The benefits of IDMF consisted in significant extension of StGrm coverage and modest increase of epidermal thickness with no inflammation (as measured by the lack of leukocytic infiltrate), para-nor hyperkeratosis. The positive control Tazarotene (a retinoid approved for psoriasis) extended coverage too, but with a trade-off of adverse effects manifesting as substantial hyperkeratosis, spongiosis and wide-spread inflammation. Lack of inflammation with IDMF was a further confirmation of our in vitro results indicating absence of skin sensitization, an effect inherent to the parent molecule, DMF.

TABLE 6

Effect of IDMF on epidermal structure in mouse tail model as compared with the Rx Tazarotene cream.

| | Test Material | | |
|---|---|---|---|
| | Control (FIG. 2A) (no treatment) | IDMF (FIG. 2B) (2% in butylene glycol/glycerin) | Tazorac (FIG. 2C) (0.1% tazarotene) |
| Tail observations > (StCr = stratum corneum) (StGrm = Stratum Granulosum) | Normal tail epidermis (3-4 layers thick, very limited stratum granulosum (StGrm). | Increase of epidermal thickness (4-5 layers), normal basketwave StCr, no inflammatory infiltrate, extended granular layer. | Marked acanthosis (8 layers) with focal spongiosis, lekocyte infiltrate, hyperkeratosis w/massive StGrm, widespread tail redness. |
| StGrm expansion | 100 (p = 1) | 134 (p < 0.0001) | 485 (p < 0.0001) |

Figure 2A:
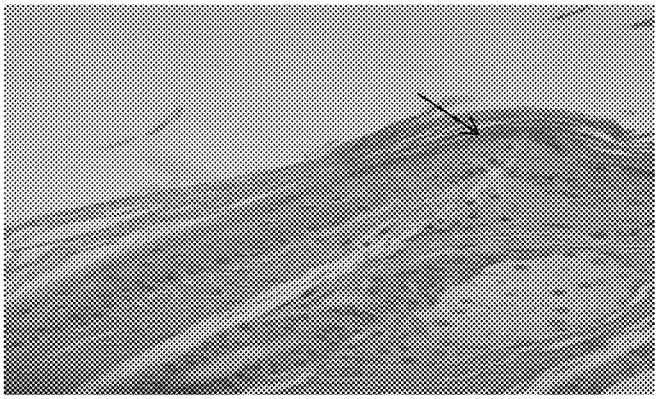
FIGS. 2A, 2B and 2C are photomicrographs of histological sections of mouse tail skin which has been treated with 2% IDMF (FIG. 2B) and Tazorac (1%)(FIG. 2C) and of a control (FIG. 2A).
Figure 2B:
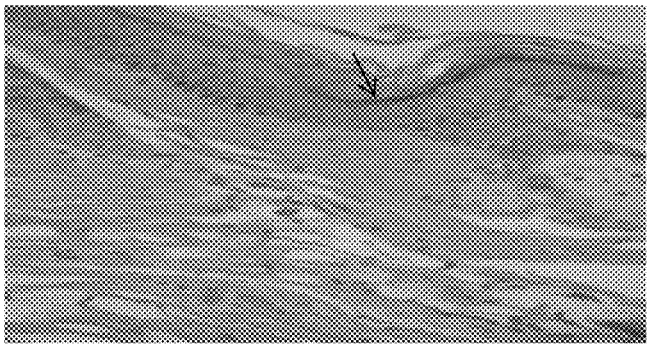
Figure 2C:
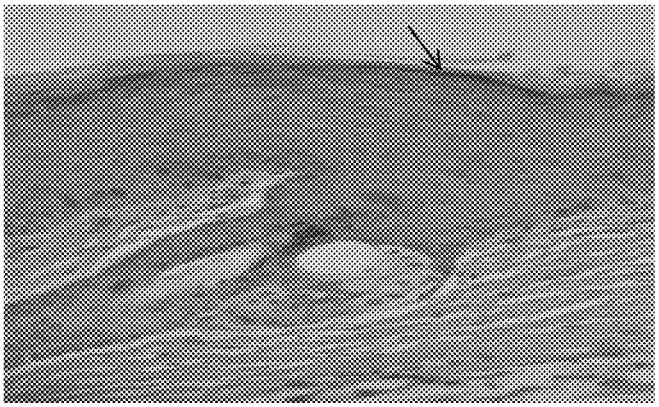

FIGS. 2A, 2B and 2C are photomicrographs (40× magnification) of H&E-stained histologic sections of the mice tail skin sections characterized in Table 6 wherein FIG. 2A shows the tail section which has not been treated and FIGS. 2A and 2B show those sections that have been treated with IDMF (2% in DMI/glycerin) and Tazarotene cream (0.1% tazarotene), respectively. The arrow in each photomicrograph points to the StGrm (stratum granulosum), which, as noted, is minimal in the control.

Example 6

Human Fibroblast Model

The DMF-like mechanism of action of IDMF was further confirmed by PCR in TNF α-treated human dermal fibroblasts (HDF). Briefly, cells cultured in DMEM/5% FBS were challenged with TNF-alpha (10 ng/ml) for 24 h, afterward test materials were added in the same medium containing TNF-alpha and incubated with HDF for another 24 h. At the end of the incubation cells were lyzed and total RNA was extracted with NucleoSpin RNA II kit (Machery-Nagel; Bethlehem, Pa.). Purified total RNA was assessed at 260 nm and 280 nm with PERKIN ELMER MBA2000 UV/VIS spectrophotometer and the concentration of RNA was equalized across all samples. cDNA was synthesized with QuantiTect Reverse Transcription kit and gene products were quantified using RealTimePrimers (Elkins Park, Pa.) primer pairs and SYBR® Premix Ex Taq™ II (Tli RNase HPlus) mastermix (Takara, Japan), with BioRad iCycler iQ Detection System. Normalization to the expression of housekeeping genes was performed to calculate fold change relative to the water control. Genes were considered differentially expressed if the level of expression was reasonably high (<30 cycles to detect) and the modulation was ≥2 fold.

It was found that both DMF (5 μg/ml) and IDMF (1 μg/ml) significantly increased (>2× fold difference) NRF2 expression and decreased NFKB expression after only 24 hours of treatment. However, surprisingly, IDMF did not increase IL8 expression and actually decreased COX-2 expression (−2.4 fold), both of which are linked to skin sensitization, evidencing a lack of skin sensitization and supporting its utility as a topical treatment.

Example 7

Safety Studies

Example 7.1

Lack of Phototoxicity in 3T3 Model (OECD)

The 3T3 Neutral Red Uptake Phototoxicity Assay was based on the OECD Guideline for Testing of Chemicals: #423, with chlorpromazine and tazarotene as positive controls. The results show that IDMF is not phototoxic even at the maximum concentration required for testing (100 μg/ml), while tazarotene and chlorpromazine had PIF>6 technically validating the assay. This suggests that in contrast to other topical drugs, such as the anti-psoriatic retinoid tazarotene, IDMF has no radiation sensitivity and is believed to be compatible with anti-psoriatic phototherapy (PUVA).

Example 7.2

Lack of Mutagenicity in the AMES Genotoxicity Model

AMES genotoxicity testing, a standard protocol for the establishment of mutagenic potential of topical actives, was conducted using MOLTOX Salmonella Mutagenicity Assay with 2 strains (TA1535, TA1537) of S. typhimurium that contain different mutations of the genes involved in histidine synthesis. Table 7 shows that IDMF was not genotoxic including at the highest concentration required for testing (5 mg/ml). As a reference, it is to be appreciated that the values are expressed as percentage (%) of the number of mutant colonies spontaneously occurring in the water control: positive control was Sodium Azide (15 μg/ml) for TA1535 and ICR 191 Acridine (10 μg/ml) for TA1537.

TABLE 7

| Mutagenicity Test | | |
|---|---|---|
| Test Material | % CTR (TA1535) | % CTR (TA1537) |
| H2O | 100 | 100 |
| DMSO | 100 | 100 |
| (+) CTR | 2161 | 18574 |
| IDMF 5 mg/ml | 18 | 13 |
| IDMF 1 mg/ml | 64 | 30 |
| IDMF 200 μg/ml | 68 | 91 |
| IDMF 40 μg/ml | 89 | 117 |
| IDMF 8 μg/ml | 96 | 83 |

Example 7.3

Lack of Skin Irritation and Sensitization in the Human RIPT

After observing beneficial anti-inflammatory activity in vitro, no inflammatory effect in the animal model and no genotoxicity, IDMF was further tested in the IRB-approved human repeat insult patch test (HRIPT) in 100 healthy adult volunteers to determine its skin irritation and sensitization potential. IDMF was formulated in a butylene glycol/glycerin base identical to the one used in animals and was tested at 2% and 5% by an independent lab (Cantor Research Laboratories, Inc., Blauvelt, N.Y., study #M-0106A and M-0106B). The test was performed accordingly to the protocol "Appraisal of the safety of Chemicals in Food, Drugs and Cosmetics" issued by FDA. It was found that on the skin sensitization/irritation scale 0-5, the IDMF formulation scored zero (0) in 100% of the participants. Interestingly, no flushing was observed with IDMF, while flushing is a key side effect of dimethyl fumarate (DMF). Therefore, the conclusion of the study was that the tested IDMF formulation was non-sensitizing and non-irritating.

The above findings and data clearly demonstrate that the novel derivative of the known anti-psoriasis drug DMF—IDMF—has DMF-like anti-psoriatic activity in vitro, and an anti-psoriatic activity in the mouse tail model, but appears to be devoid of the skin sensitization effects characteristic of its parent molecule. Accordingly, these finding show that IDMF and the related compounds as disclosed herein provide a new, powerful anti-psoriasis drug. It also demonstrates that these compositions may be applied or administered topically thereby also avoiding DMF's serious systemic side effects.

It should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof. In following, from the foregoing description, various modifications and changes in the compositions and methods of this disclosure will occur to those skilled in the art and all such modifications are within the scope of the present teaching and are intended to be included therein.

We claim:

[1. A compound according to the general formula (I):

(I)

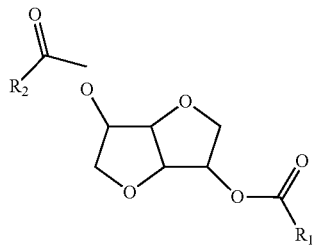

in which $R_1$ and $R_2$ are both —CH═CH—COOMe or one of $R_1$ and $R_2$ are H and the other —CH═CH—COOMe.]

[2. The compound of claim 1 wherein $R_1$ and $R_2$ are the same.]

[3. The compound of claim 1 wherein $R_1$ and $R_2$ are not the same.]

4. A pharmaceutical composition comprising one or more compounds of [claim 1 in a pharmaceutically acceptable vehicle] *formula (I)*

(I)

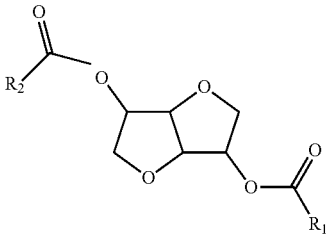

*in which $R_1$ and $R_2$ are both —CH═CH—COOMe or one of $R_1$ and $R_2$ is H and the other —CH═CH—COOMe, in a pharmaceutically acceptable vehicle.*

5. The pharmaceutical composition of claim 4 wherein $R_1$ and $R_2$ are the same.

6. The pharmaceutical composition of claim 4 wherein $R_1$ and $R_2$ are not the same.

7. The pharmaceutical composition of claim 4 further comprising at least one other pharmaceutical active.

8. The pharmaceutical composition of claim 7 wherein the at least one other pharmaceutical active is one or more compounds corresponding to the formula II or formula III or at least one of each:

(II)

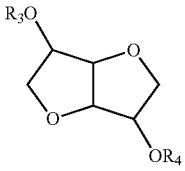

(III)

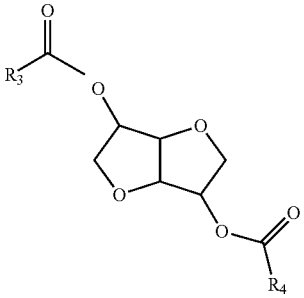

wherein $R_3$ and $R_4$ which are the same or different, are independently selected from straight chain or branched; saturated or unsaturated alkyl groups having from 4 to 30 carbon atoms provided that when $R_3$ and $R_4$ are different, one of $R_3$ or $R_4$ is hydrogen or a straight chain or branched, saturated or unsaturated alkyl group of from 1 to 30 carbon atoms.

9. The pharmaceutical composition of claim 8 wherein the additional pharmaceutical active is of formula Ill and the alkyl groups of $R_3$ and $R_4$ have from 16 to 18 carbon atoms.

10. The pharmaceutical composition of claim 8 wherein the additional pharmaceutical active is isosorbide dilinoleate.

11. A method of therapeutically treating psoriasis comprising administering to the patient suffering therefrom an effective amount of a compound according to formula [1] (*I*)

(I)

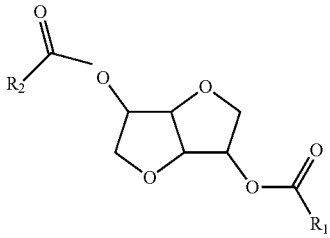

*in which $R_1$ and $R_2$ are both —CH═CH—COOMe or one of $R_1$ and $R_2$ is H and the other —CH═CH—COOMe.*

12. The method of claim 11 wherein $R_1$ and $R_2$ are the same.

13. The method of claim 11 wherein $R_1$ and $R_2$ are not the same.

14. The method of claim 11 wherein the compound is a component of a pharmaceutical composition that is administered to the patient.

15. The method of claim 14 wherein the pharmaceutical composition is administered orally.

16. The method of claim 14 wherein the pharmaceutical composition is applied topically to those areas of the skin of a patient manifesting symptoms of psoriasis.

17. The method of claim 14 wherein the pharmaceutical composition further comprises at least one other pharmaceutical active.

18. The method of claim 17 wherein the at least one other pharmaceutical active is one or more compounds corresponding to the formulae II and/or III:

(II)

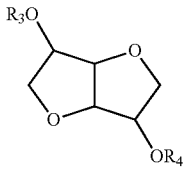

(III)

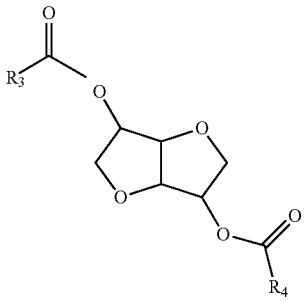

wherein $R_3$ and $R_4$ which are the same or different, are independently selected from straight chain or branched; saturated or unsaturated alkyl groups having from 4 to 30 carbon atoms provided that when $R_3$ and $R_4$ are different, one of $R_3$ or $R_4$ is hydrogen or a straight chain or branched, saturated or unsaturated alkyl group of from 1 to 30 carbon atoms.

19. The method of claim 18 wherein the additional pharmaceutical active is of formula III and the alkyl groups of $R_3$ and $R_4$ have from 16 to 18 carbon atoms.

20. The method of claim 17 wherein the additional pharmaceutical active is isosorbide dilinoleate.

21. A method of delaying the onset of symptoms of psoriasis in persons predisposed to the disease comprising administering to said persons a therapeutically effective amount of a compound according to formula [1] (*I*)

(I)

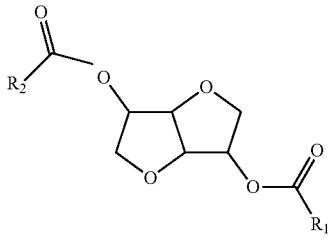

*in which $R_1$ and $R_2$ are both —CH═CH—COOMe or one of $R_1$ and $R_2$ is H and the other —CH═CH—COOMe.*

*22. The pharmaceutical composition of claim 4 wherein the one or more compounds according to the general formula (I) is or includes isosorbide di(methylfumarate)*

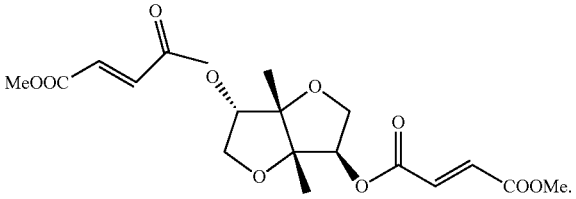

*23. The pharmaceutical composition of claim 4 wherein the one or more compounds according to the general formula (I) are isosorbides.*

*24. The method of claim 11 wherein the compound of according to he general formula (I) is isosorbide di-(methylfumarate)*

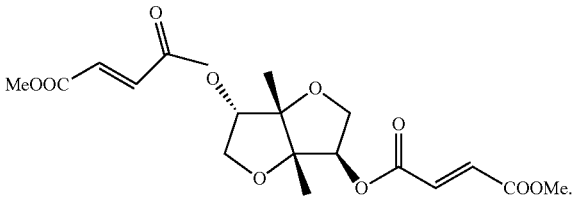

*25. The pharmaceutical composition of claim 4 wherein the one or more compounds according to the general formula (I) is the combination of isosorbide di-(methylfumarate) and isosorbide mono-(methylfumarate) each formed by the reaction of methyl fumarate and/or fumaric acid and isosorbide.*

* * * * *